(12) United States Patent
Sun et al.

(10) Patent No.: US 8,970,842 B2
(45) Date of Patent: Mar. 3, 2015

(54) MULTI-HARMONIC INLINE REFERENCE CELL FOR OPTICAL TRACE GAS SENSING

(71) Applicants: Kang Sun, Princeton, NJ (US); Lei Tao, Plainsboro, NJ (US); David Miller, Princeton, NJ (US); M. Amir Khan, Plainsboro, NJ (US); Mark A. Zondlo, Princeton, NJ (US)

(72) Inventors: Kang Sun, Princeton, NJ (US); Lei Tao, Plainsboro, NJ (US); David Miller, Princeton, NJ (US); M. Amir Khan, Plainsboro, NJ (US); Mark A. Zondlo, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 13/967,675

(22) Filed: Aug. 15, 2013

(65) Prior Publication Data

US 2014/0049777 A1 Feb. 20, 2014

Related U.S. Application Data

(60) Provisional application No. 61/683,536, filed on Aug. 15, 2012.

(51) Int. Cl.
| | |
|---|---|
| *G01N 21/00* | (2006.01) |
| *G01J 3/42* | (2006.01) |
| *G01J 3/28* | (2006.01) |
| *G01J 3/433* | (2006.01) |
| *G01N 21/3504* | (2014.01) |

(Continued)

(52) U.S. Cl.
CPC .... *G01J 3/42* (2013.01); *G01J 3/28* (2013.01); *G01J 3/4338* (2013.01); *G01N 21/3504* (2013.01); *G01N 21/274* (2013.01); *G01N 21/39* (2013.01); *G01N 2021/399* (2013.01)

USPC .......................................... 356/433; 356/432

(58) Field of Classification Search
CPC ........................ G01N 21/3504; G01N 21/1702
USPC .................................................. 356/432–444
See application file for complete search history.

(56) References Cited

U.S. PATENT DOCUMENTS

| 5,332,901 A | * | 7/1994 | Eckles et al. | 250/345 |
| 5,459,574 A | * | 10/1995 | Lee et al. | 356/437 |

(Continued)

OTHER PUBLICATIONS

F. Schreier, "The Voigt and Complex Error Function: A Comparison of Computational Methods," Journal of Quan. Spectroscopy & Radiative Transfer vol. 48, No. 5/6; 743-762 (1992).

(Continued)

*Primary Examiner* — Tri T Ton
(74) *Attorney, Agent, or Firm* — Meagher Emanuel Laks Goldberg & Liao, LLP

(57) ABSTRACT

A spectroscopic sensor and a spectroscopic method of determining a concentration of a sample are disclosed. The sensor is used in connection with a sample cell containing a sample. The sensor includes a coherent light source configured to transmit an interrogation light beam along an optical sample path directed towards the sample. The sensor also includes an in-line reference cell located in the sample path. The sensor also includes a detector having outputs responsive to absorption signals from the sample and the in-line reference cell. The sensor also includes a processor configured to isolate the reference absorption signals from the in-line reference cell and sample absorption signals from the sample cell and generate calibration information based on the reference absorption signals and determine a concentration of the sample based on the sample absorption signals.

22 Claims, 17 Drawing Sheets

(51) Int. Cl.
  G01N 21/27 (2006.01)
  G01N 21/39 (2006.01)

(56) References Cited

U.S. PATENT DOCUMENTS

2012/0287418 A1* 11/2012 Scherer et al. .................. 356/51
2013/0250304 A1* 9/2013 Burba ........................... 356/437

OTHER PUBLICATIONS

J. Seufert, et al. "DFB laser diodes in the wavelength range from 760 nm to 2.5 μm," Spectrochimica Acta—Part A 60; 3243-3247 (2004).
J. A. Silver, "Simple dense-pattern optical multipass cells," Applied Optics vol. 44, No. 31; 6545-6556 (Nov. 1, 2005).
L. Tao, K. Sun, D. J. Miller, M. A. Khan, and M. A. Zondlo, "Current and frequency modulation characteristics for continuous-wave quantum cascade lasers at 9.06 μm," Optic Letters vol. 37, No. 8; 1358-1360 (Apr. 15, 2012).
H. Teichert, T. Fernholz, and V. Ebert, "Simultaneous in situ measurement of CO, H2O, and gas temperatures in a full-sized coal-fired power plant by near-infrared diode lasers," Applied Optics vol. 42, No. 12; 2043-2051 (Apr. 20, 2003).
A. Vicet, et al. "Trace gas detection with antimonide-based quantum-well diode lasers," Spectrochimica Acta—Part A 58; 2405-2412 (2002).
H. Volten, et al. "Two instruments based on differential optical absorption spectroscopy (DOAS) to measure accurate ammonia concentrations in the atmosphere," Atmos. Meas. Tech. 5; 413-427 (Feb. 21, 2012).
K. Von Bobrutzki, et al. "Field inter-comparison of eleven atmospheric ammonia measurement techniques," Atmos. Meas. Tech. Discuss. 2; 1783-1835 (Aug. 4, 2009).
J. Wang, et al. "In situ combustion measurements of CO with diode-laser absorption near 2.3 μm," Applied Optics vol. 39, No. 30; 5579-5589 (Oct. 20, 2000).
R. A. Whitby, and E. R. Altwicker, "Acetylene in the Atmosphere: Sources, Representative Ambient Concentrations and Ratios to other Hydrocarbons," Atmos. Enviornment vol. 12; 1289-1296 (1977).
J. D. Whitehead, I. D. Longley, and M. W. Gallagher, "Seasonal and Diurnal Variation in Atmospheric Ammonia in an Urban Environment Measured Using a Quantum Cascade Laser Absorption Spectrometer," Water Air Soil Pollut. 183; 317-329 (Apr. 3, 2007).
G. V. H. Wilson, "Modulation Broadening of NMR and ESR Line Shapes," Journal of App. Physics vol. 34, No. 11; 3276-3285 (Nov. 1963).
V. Zeninari, et al. "Laboratory spectroscopic calibration of infrared tunable laser spectrometers for the in situ sensing of the Earth and Martian atmospheres," Applied Physics B—Lasers and Optics 85; 265-272 (2006).
D. Zona, et al. "Impact of extreme precipitation and water table change on N2O fluxes in a bio-energy poplar plantation," Biogeosciences Discussions 8; 2057-2092 (Mar. 2, 2011).
M. A. Zondlo, M. E. Paige, S. M. Massick, and J. A. Silver, "Vertical cavity laser hygrometer for the National Science Foundation Gulfstream—V aircraft," Journal of Geophys. Research vol. 115, D20309; 1-14 (Oct. 29, 2010).
P. Werle, R. Miicke, and F. Slemr, "The Limits of Signal Averaging in Atmospheric Trace-Gas Monitoring by Tunable Diode-Laser Absorption Spectroscopy (TDLAS)," Applied Physics B 57; 131-139 (1993).
J. B. McManus, P.L. Kebabian, and M. S. Zahniser, "Astigmatic mirror multipass absorption cells for long-path-length spectroscopy," Applied Optics vol. 34, No. 18; 3336-3348 (Jun. 20, 1995).
J. Dick. U. Skiba, and J. Wilson, "The Effect of Rainfall on NO and N2O Emissions from Ugandan Agroforest Soils," Phyton-Ann Rei. Bota. vol. 41; 73-80 (2001).
J. Chen, A. Hangauer, R. Strzoda, and M. C. Amann, "VCSEL-based calibration-free carbon monoxide sensor at 2.3 μm with in-line reference cell," Applied Physics B—Lasers and Optics 102; 381-389 (2011).

V. P. Aneja, W. H. Schlesinger, and J. W. Erisman, "Farming Pollution," Nature Geosci. vol. 1; 409-411 (Jul. 2008).
R. Arndt, "Analytical Line Shapes for Lorentzian Signals Broadened by Modulation," Journal of App. Physics vol. 36, No. 8; 2522-2524 (Aug. 1965).
D. R. Benson, A. Markovich, M. Al-Refai, and S.-H. Lee, "A Chemical Ionization Mass Spectrometer for ambient measurements of Ammonia," Atmos. Meas. Tech. 3; 1075-1087 (Aug. 19, 2010).
R. Bobbink, K. Hicks, J. Galloway, T. Spranger, R. Alkemade, M. Ashmore, M. Bustamante, S. Cinderby, E. Davidson, F. Dentener, B. Emmett, J.-W. Erisman, M. Fenn, F. Gilliam, A. Nordin, L. Pardo, and W. De Vries, "Global assessment of nitrogen deposition effects on terrestrial plant diversity: a synthesis," Eco. Apps. vol. 20, No. 1; 30-59 (2010).
G. Boehm, M.Graub, O. Diera, K. Windhomb, E. Roenneberg, J. Rosskopfb, R. Shaub, R. Meyera, M. Orstsieferb, and M.-C. Amann, "Growth of InAs-containing quantum wells for InP-based VCSELs emitting at 2.3 mm," Journal of Crystal Growth 301-302; 941-944 (2007).
J. Chen, A. Hangauer, R. Strzoda, and M.-C. Amann, "Experimental characterization of the frequency modulation behavior of vertical cavity surface emitting lasers," App. Physics Letters 91; 141105 (2007).
J. Chen, A. Hangauer, R. Strzoda, and M.-C. Amann, "Tunable diode laser spectroscopy with optimum wavelength scanning," Applied Physics B—Lasers and Optics 100; 331-339 (2010).
J. Chen, A. Hangauer, R. Strzoda, and M.-C. Amann, "Accurate extraction method for the FM response of tunable diode lasers based on wavelength modulation spectroscopy," Applied Physics B—Lasers and Optics 90; 243-247 (2008).
D. W. Allan, "Statistics of Atomic Frequency Standards," Proceedings of the IEEE vol. 54, No. 2; 221-230 (Feb. 1966).
A. De Gouw, et al. "Airborne Measurements of Ethene from Industrial Sources Using Laser Photo-Acoustic Spectroscopy," Environ. Sci. Technol. vol. 43, No. 7; 2437-2442 (2009).
A. N. Dharamsi, and Y. Lu, "Sensitive density-fluctuation measurements using wavelength-modulation spectroscopy with high-order-harmonic detection," Applied Physics B—Lasers and Optics 62; 273-278 (1996).
A. N. Dharamsi, and A. M. Bullock, "Applications of wavelength-modulation spectroscopy in resolution of pressure and modulation broadened spectra," Applied Physics B—Lasers and Optics 63; 283-292 (1996).
V. Ebert, H. Teichert, P. Strauch, T. Kolb, H. Seifert, and J. Wolfrum, "Sensitive in situ detection of CO and O2 in a rotary kiln-based hazardous waste incinerator using 760 nm and new 2.3 μm diode lasers," Proceedings of the Combustion Institute 30; 1611-1618 (2005).
R. A. Ellis, et al. "Characterizing a Quantum Cascade Tunable Infrared Laser Differential Absorption Spectrometer (QC-TILDAS) for measurements of atmospheric ammonia," Atmos. Meas. Tech. 3; 397-406 (2010).
I. Gong, R. Lewicki, R. J. Griffin, J. H. Flynn, B. L. Lefer, and F.K. Tittel, "Atmospheric ammonia measurements in Houston, TX using an external-cavity quantum cascade laser-based sensor," Atmos. Chem. Phys. 11; 9721-9733 (Sep. 20, 2011).
C. Guimbaud, et al. "A portable infrared laser spectrometer for flux measurements of trace gases at the geosphere-atmosphere interface," Meas. Sci. Technol. 22; 1-17 (May 20, 2011).
M. Guinet, P. Jeseck, D. Mondelain, I. Pepin, C. Janssen, C. Camy-Peyret, and J. Y. Mandin, "Absolute measurements of intensities, positions and self-broadening coefficients of R branch transitions in the v2 band of ammonia," Journal of Quan. Spectroscopy and Radiative Transfer 112; 1950-1960 (2011).
L. Bernstein, et al. "Climate Change 2007: Synthesis Report. Contribution of Working Groups I, II, and III to the Fourth Assessment Report of the Intergovernmental panel on Climate Change," IPCC Plenary XXVII, 26-73 (Nov. 2007).
L. Joly, et al. "Development of a versatile atmospheric N2O sensor based on quantum cascade laser technology at 4.5 μm," Applied Physics B—Lasers and Optics, 103; 717-723 (2011).

(56) References Cited

OTHER PUBLICATIONS

I. Kleiner, "NH3 and PH3 line parameters: the 2000 HITRAN update and new results," Journal of Quan. Spectroscopy & Radiative Transfer, 82; 293-312 (2003).

P. Kluczynski, J. Gustafsson, A. M. Lindberg, and O. Axner, "Wavelength modulation absorption spectrometry—an extensive scrutiny of the generation of signals," Spectrochimica Acta—Part B, 56; 1277-1354 (2001).

W. C. Kuster, F. J. M. Harren, and J. A. De Gouw, "Inter-comparison of Laser Photoacoustic Spectroscopy and Gas Chromatography Techniques for Measurements of Ethene in the Atmosphere," Enviorn. Sci. Technol. vol. 39, No. 12; 4581-4585 (2005).

Y. Li, J. J. Schwab, and K. L. Demerjian, "Measurements of ambient ammonia using a tunable diode laser absorption spectrometer: Characteristics of ambient ammonia emissions in an urban area of New York City," Journal of Geophys. Research vol. 3, D10S02; 1-11 (May 17, 2006).

H. Li, G. B. Rieker, X. Liu, J. B. Jeffries, and R. K. Hanson, "Extension of wavelength-modulation spectroscopy to large modulation depth for diode laser absorption measurements in high-pressure gases," Applied Optics vol. 45, No. 5; 1052-1061 (Feb. 10, 2006).

J. P. Lima, H. Vargas, A. Miklos, M. Angelmahr, and P. Hess, "Photoacoustic detection of NO2 and N2O using quantum cascade lasers," Applied Physics B—Lasers and Optics 85; 279-284 (2006).

J. Li, U. Parchatka, R. Konlgstedt, and H. Fischer, "Real-time measurements of atmospheric CO using a continuous-wave room temperature quantum cascade laser based spectrometer," Optics Express vol. 20, No. 7; 7591-7601 (Mar. 26, 2012).

Y. Liu, M. Shao, S. Lu, C.- C. Chang, J.- L. Wang, and G. Chen, "Volatile Organic Compound (VOC) measurements in the Pearl River Delta (PRD) region, China," Atmos. Chem. Phys. 8; 1531-1545 (Mar. 13, 2008).

A. Lytkine, W. Jager, and J. Tulip, "Frequency tuning of long-wavelength VCSELs," Spectrochimica Acta—Part A 63; 940-946 (2006).

J. Manne, O. Sukhorukov, W. Jager, and J. Tulip, "Pulsed quantum cascade laser-based cavity ring-down spectroscopy for ammonia detection in breath," Applied Optics vol. 45, No. 36; 9230-9237 (Dec. 20, 2006).

A. McDermitt, et al. "A new low-power, open-path instrument for measuring methane flux by eddy covariance," Applied Physics B—Lasers and Optics 102; 391-405 (2011).

J.- C. Nicolas, A. N. Baranov, Y. Cuminal, Y. Rouillard, and C. Alibert, "Tunable diode laser absorption spectroscopy of carbon monoxide around 2.35 μm," Applied Optics, vol. 37, No. 33; 7906-7911 (Nov. 20, 1998).

J. B. Mamanus, et al. "Pulsed quantum cascade laser instrument with compact design for rapid, high sensitivity measurements of trace gases in air," Applied Physics B—Lasers and Optics 92; 387-392 (2008).

Z. Y. Meng, et al. "Characteristics of atmospheric ammonia over Beijing, China," Atmos. Chem Phys. 11; 6139-6151 (Jun. 29, 2011).

D. J. Miller, and M. A . Zondlo, "Open-Path High Sensitivity Atmospheric Ammonia Sensing with a 9 μm Quantum Cascade Laser," Optical Society of America/CLEO/QELS; (2010).

K. Mohan, M. A. Khan, and A. N. Dharamsi, "Characterization of lineshape structure by wavelength modulation spectroscopy," Applied Physics B—Lasers and Optics 102; 569-578 (2010).

D. J. Miller, et al. "Open-path, quantum cascade laser-based sensor for high resolution atmospheric ammonia measurements," Atmos. Meas. Tech. Discuss. 6; 7005-7039 (Jul. 31, 2013).

S. A. Montzka, E. J. Dlugokencky, and J. H. Butler, "Non-CO2 greenhouse gases and climate change," Nature, vol. 476; 43-50 (Aug. 4, 2011).

A. Neftel, et al. "Experimental assessment of N2O background fluxes in grassland systems," The Authors Journal Compilation 59B; 470-482 (2007).

A. Neftel, et al. "N2O exchange over managed grassland: Application of a quantum cascade laser spectrometer for micrometeorological flux measurements," Agricultural and Forest Meteorology 150; 775-785 (2010).

A. Khan, et al. "Simultaneous detection of atmospheric nitrous-oxide and carbon-monoxide using a quantum-cascade laser," Proc. of SPIE vol. 8029; (May 13, 2011).

J. B. Nowak, et al. "Airborne observations of ammonia and ammonium nitrate formation over Houston, Texas," Journal of Geophys. Research vol. 115, D22304; 1-12 (Nov. 23, 2010).

R. W. Pinder, A. B. Gilliland, and R. L. Dennis, "Environmental impact of atmospheric NH3 emissions under present and future conditions in the eastern United States," Geophys. Research Letters vol. 35, L12808; 1-6 (Jun. 25, 2008).

R. Pohle, et al. "Fire detection with low power fet gas sensors," Sensors and Actuators B 120; 669-672 (2007).

R. Provencal, et al. "Cavity-enhanced quantum-cascade laser-based instrument for carbon monoxide measurements," Applied Optics vol. 44, No. 31; 6712-6717 (Nov. 1, 2005).

A. R. Ravishankara, J. S. Daniel, R. W. Portmann, "Nitrous Oxide (N2O): The Dominant Ozone-Depleting Substance Emitted in the 21st Century," Science vol. 326; 123-125 (Oct. 2, 2009).

J. Reid, and D. Labric, "Second Harmonic Detection with Tunable Diode Lasers Comparison of Experiment and Theory," Applied Physics B 26; 203-210 (1981).

G. B. Rieker, J. B. Jeffries, and R. K. Hanson, "Calibration-free wavelength-modulation spectroscopy for measurements of gas temperature and concentration in harsh environments," Applied Optics vol. 48, No. 29; 5546-5560 (Oct. 10, 2009).

L. S. Rothman, et al. "The HITRAN 2008 molecular spectroscopic database," Journal of Quan. Spectroscopy & Radiative Transfer 110; 533-572 (2009).

S. Schilt, and L. Thevenaz, "Experimental method based on wavelength-modulation spectroscopy for the characterization of semiconductor lasers under direct modulation," Applied Optics vol. 43, No. 22; 4446-4453 (Aug. 1, 2004).

\* cited by examiner

MULTI-HARMONIC INLINE REFERENCE CELL FOR OPTICAL TRACE GAS SENSING

CROSS-REFERENCE TO PRIOR FILED APPLICATIONS

This application claims priority to U.S. provisional application 61/683,536 which was filed on Aug. 15, 2012 which is incorporated herein in its entirety.

GOVERNMENT RIGHTS IN THIS INVENTION

This invention was made with government support under Grant #EEC-0540832 awarded by the National Science Foundation. The government has certain rights in this invention.

TECHNICAL FIELD

This invention relates generally to systems and methods to calibrate, account for system drift, and determine system noise in real-time for laser-based trace gas sensing.

BACKGROUND

Conventional calibration methods using laser-based trace gas sensors require either separate reference cells or interrupt the measurement to calibrate. In the former, the optical pathlengths of the sample gas and reference cell will have different characteristics including optical fringes, sensitivities, and environmental conditions. All of these factors may complicate the relevance of the reference cell calibration to the sampled gas. The latter technique only provides an intermittent calibration method and thereby stops the measurement intrinsically and requires frequent calibrations under rapidly changing conditions. It would be desirable to provide systems and methods that address these and other shortcomings of existing systems.

SUMMARY OF THE INVENTION

A spectroscopic sensor and a spectroscopic method of determining a concentration of a sample are disclosed. The sensor is used in connection with a sample cell containing a sample. The sensor includes a coherent light source configured to transmit an interrogation light beam along an optical sample path directed towards the sample. The sensor also includes an in-line reference cell located in the sample path. The sensor also includes a detector having outputs responsive to absorption signals from the sample and the in-line reference cell. The sensor also includes a processor configured to isolate the reference absorption signals from the in-line reference cell and sample absorption signals from the sample cell and generate calibration information based on the reference absorption signals and determine a concentration of the sample based on the sample absorption signals.

The sensor may also include circuitry configured to tune the coherent light source across an absorption range of interest. The coherent light source may be scanned across the absorption range at a lower frequency and modulated at a higher frequency. The coherent light source may be a quantum cascade laser, interband cascade laser, vertical cavity laser or semiconductor laser. The in-line reference cell may be a closed path, in-line reference cell configured with angled windows or windows with an anti-reflective coating to minimize back reflections from the windows. The reference absorption signals may be offset spectrally from the sample absorption signals.

The reference cell may have a pressure of less than atmospheric pressure. The reference cell may have a pressure of approximately 0.1 atmospheres. The sample cell may include an optical cavity with an optical path length configured to measure the gas of interest at ambient conditions. The processor may be configured to analyze a harmonic of the reference absorption signals. The processor may be configured to analyze a sixth or greater harmonic of reference absorption signals. The processor may be configured to analyze a harmonic of the sample absorption signals. The processor may be configured to analyze a second harmonic of the sample absorption signals.

A spectroscopic method of determining a concentration of a sample cell containing a sample is disclosed. The method includes providing a coherent light source configured to transmit an interrogation light beam along an optical sample path directed towards the sample. The method also includes locating an in-line reference cell in the sample path. The method also includes detecting absorption signals from the sample and the in-line reference cell. The method also includes isolating reference absorption signals from the in-line reference cell and sample absorption signals from the sample cell, generating calibration information based on the reference absorption signals and determining a concentration of the sample based on the sample absorption signals.

The coherent light source may be tuned across an absorption range of interest and scanning the coherent light source across the absorption range at a lower frequency and modulating the coherent light source at a higher frequency. The coherent light source may be a quantum cascade laser, interband cascade laser, vertical cavity laser or semiconductor laser. The in-line reference cell may be a closed path, in-line reference cell configured with angled windows or windows with an anti-reflective coating to minimize back reflections from the windows. The reference absorption signals may be offset spectrally from the sample absorption signals.

The reference cell may have a pressure of less than atmospheric pressure. The reference cell may have a pressure of approximately 0.1 atmospheres. The sample cell may include an optical cavity with an optical path length configured to measure the gas of interest at ambient conditions. The processor may be configured to analyze a harmonic of the reference absorption signals. The processor may be configured to analyze a sixth or greater harmonic of reference absorption signals. The processor may be configured to analyze a harmonic of the sample absorption signals. The processor may be configured to analyze a second harmonic of the sample absorption signals.

DETAILED DESCRIPTION

Figure 1A:
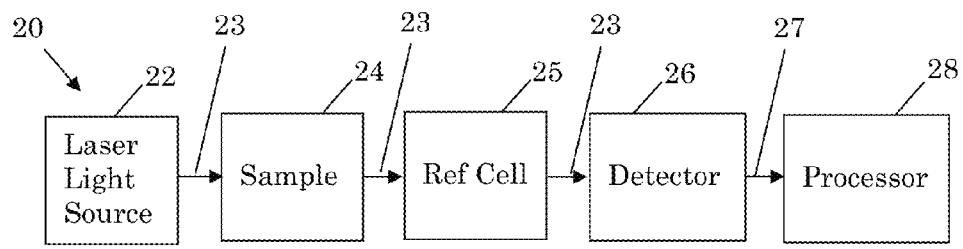
FIG. 1a is a general system block diagram.

The disclosed process and apparatus provides more accurate measurements of trace gases from laser-based optical sensors. The disclosed process and apparatus has applications in environmental monitoring, industrial sensing, and biomedical gas sensing. Immediate uses include those gases that require open-path measurements such as long-path or integrated measurements, fenceline monitoring, or gases that cannot be sampled easily into a controlled environment. While the disclosed process and apparatus can be used in either open-path (ambient) or closed path configurations, it is particularly well-suited for sensing under ambient conditions where absorption features are broadened and overlap with one another.

The disclosed process and apparatus has the ability to calibrate a targeted gas online and in-situ without a separate optical reference path or requiring off-line calibration techniques. Conventional calibration methods using laser-based trace gas sensors require either separate reference cells or interrupt the measurement to calibrate. In the former, the optical pathlengths of the sample gas and reference cell will have different characteristics including optical fringes, sensitivities, and environmental conditions. All of these factors may complicate the relevance of the reference cell calibration to the sampled gas. The latter technique only provides an intermittent calibration method and thereby stops the measurement intrinsically and requires frequent calibrations under rapidly changing conditions.

The disclosed process and apparatus calibrates and accounts for system drift and determines precision and noise characteristics of the laser-based trace gas measurement. The process uses multiharmonic wavelength modulation spectroscopy with an in-line reference cell to measure the target sample gas and reference gas at the same time. First, an in-line reference cell is placed in the sample optical train. Next, the in-line reference cell is filled at a known concentration and pressure of a select gas (or gases) of interest. The reference cell gas is selected by identifying a gas that has an absorption feature that is capable of being scanned by the same laser. The reference cell absorption feature is distinguished from the ambient trace gas absorption feature through the use of multiharmonic wavelength modulation spectroscopy. Different modulation indices, amplitudes, and harmonic spectra are used to differentiate the target gas signal from the reference gas signal. The reference signal is used as a calibration standard that accounts for systematic drift, and quantifies the noise properties of the overall sensor.

The introduction of the in-line reference cell will introduce optical fringes to the system, which can be minimized by anti-reflection coatings or wedged windows. For high-precision measurements, the temperature of the reference cell should be known. This approach was tested with an open-path ammonia sensor using ethylene as the reference gas. The disclosed process and apparatus was also used in an open-path ammonia sensor, nitrous oxide sensor, and methane sensor.

The disclosed process and apparatus can be used to calibrate trace gas sensors in real-time and in conditions where conventional calibration techniques are limited (rapidly changing sample conditions, open-path designs, systems with a separate reference optical path). It is especially relevant for applications of high-precision trace gas monitoring where even slight changes in ambient conditions may change the sensor response and calibration.

In general, a typical spectroscopic system works as follows. Assume we have a reference absorption signal A (from gas A) is inside the in-line reference cell. Also assume we have a sample absorption signal B (from gas B) from a gas of interest in a sample cell (e.g. in the atmosphere). Gas A is chosen such that it has absorption features that can also be observed while also probing the spectroscopic feature of interest in gas B. In conventional spectroscopic approaches, signals A and B will interfere with one another. In other words, as the concentration of gas of interest B increases, its absorption signal will increase, and this will affect the nominal reference signal A. Thus, because reference absorption signal from A is influenced by the sample absorption signal from B (which currently is unknown since this is the signal being measured), such an approach will not work.

In contrast, the approach disclosed herein is to use the above configuration (in-line reference cell) with multiharmonic wavelength modulation spectroscopy to separate out signals A and B. Wavelength modulation spectroscopy (WMS) is a common technique. WMS can be thought of as a derivative of the absorption spectrum. In other words, the second derivative of the absorption profile would be the second harmonic signal (spectrum). The second harmonic, or 2f signal may be used in WMS. As one goes to higher and higher harmonics, two absorption lines that lie close together will eventually be observed independently from one another. But, as one goes to higher harmonics, the signal-to-noise ratio gets progressively worse. So just analyzing on signal at a high harmonic and the other signal at a lower harmonic does not work. Indeed, one would probably have to go to very high differences in harmonics just to separate out two signals of similar spectral widths.

In order to address these issues, the disclosed approach uses a reduced pressure cell for the in-line reference signal. This reference absorption signal A (and subsequent harmonics or derivatives) is much narrower than the gas of interest B, usually with B at ambient (air-broadened) pressures. By analyzing the higher harmonic signals on the reference A signal, one can get an independent measure of it—which at higher and higher derivatives becomes constant (i.e. B becomes negligible). In other words, as the ambient signal B goes up or down, the reference signal A stays constant because the tailing baseline of signal B is basically a zero (negligible) baseline when viewed at higher harmonics (derivatives). By relating spectroscopic principles to the relationship between A and B, one can then calibrate the signal B (e.g. peak height of 2f signal) by its relative signal to A (e.g. peak height of 10f signal).

In systems configured for detection of ammonia, we use between the 6th and 12th harmonics (derivative-like) signals of the in-line reference signal of ethylene (A). Changes in ammonia (B) do not affect the in-line ethylene signal (A). This is because the reduced-pressure ethylene signal is narrower than the broad, atmospheric signal of ammonia. In addition, a much higher harmonic signal is analyzed from the in-line reference cell than the ammonia signal. The ammonia signal is essentially a sloping baseline on the reference ethylene signal. By going to higher and higher harmonics (derivatives), what happens is that the ammonia signal eventually has no influence whatsoever on the reference signal. The system can then relate the nth harmonic signal of ethylene (A) to the 2f (most common) signal of ammonia (B). The ratio of the nth-derivative of A to the 2nd derivative of B is defined by spectroscopic parameters. Thus, as the A/B ratio changes, we can determine the actual concentration of B under all conditions, all the time.

Atmospheric ammonia ($NH_3$) is a key component in the global nitrogen cycle. As the dominant alkaline atmospheric species, ammonia reacts readily with atmospheric acidic species such as sulfuric acid ($H_2SO_4$) and nitric acid ($HNO_3$) to form ammoniated aerosols, with strong implications for regional air quality and global radiative forcing. Ammonia also plays an important role in the deposition of reactive nitrogen in sensitive ecosystems. Despite the importance of atmospheric ammonia, its spatial and temporal variability are poorly characterized due to its low atmospheric concentration and high reactivity.

Traditional ammonia measurements utilize passive filters and denuders with long integration times, and they are usually labor-intensive in operation and maintenance. State-of-the-art techniques include chemical ionization mass spectrometry (CIMS), laser direct absorption spectroscopy, photoacoustic spectroscopy, and cavity ring down spectroscopy. All of these techniques need to sample ammonia into a closed-path system and thus involve direct contact with sampling surface to which ammonia readily adsorbs. Closed-path measurements of ammonia are complicated by significant backgrounds, unknown buffering of large changes in concentration and ambiguity between ammonia and ammonium due to phase transitions in sampling lines. For field deployments where conditions can change rapidly, the simplicity and automation of calibration needs improvement at typical ambient concentrations (parts per billion by volume (ppbv) level).

To address the sampling issue of closed-path techniques, the disclosed process and apparatus is directed to an open-path ammonia sensor using a quantum cascade laser (QCL) operating at 9.06 μm for atmospheric measurements. Wavelength modulation spectroscopy (WMS) is used to enhance the signal to noise ratio (SNR) and resolve air-broadened absorption lines. Given the complexity of WMS systems, calibrations with reference samples are widely used to make accurate measurements. However, the same problem with the calibration of a closed-path ammonia sensor remains for an open-path sensor: one needs to introduce a known concentration of ammonia for calibration. Ethylene ($C_2H_4$) has an abundance of absorption lines in the v7 band near the ammonia v2 band in mid-infrared spectral region. Previous research has shown that ethylene can be used in ammonia sensors as a reference of laser wavelength at 10.34 μm and as a reference for ammonia concentration calibration at 9.06 μm. Disclosed herein is a new in-situ calibration method with an inline ethylene reference cell by using multi-harmonic WMS. Ethylene is a stable, relatively inert gas and has line strengths two orders of magnitude smaller than ammonia near 9.06 μm. Thus ethylene does not cause interference at typical atmospheric mixing ratios (sub-ppbv), which are comparable to ammonia mixing ratios. At a low pressure (<100 hPa), high gas concentration (1%), and short path length (~10 cm), ethylene shows a stable absorption signal partially offset from the ammonia absorption feature, and the ethylene signal can serve as a reference for ammonia concentration in real time. This calibration method can also compensate for the effect of laser drifting by line locking to the sharp ethylene peak instead of the air-broadened ammonia peak, which is particularly useful near the detection limit.

Comparing to conventional WMS, the disclosed process and apparatus has advantages in accuracy, frequency, simplicity, and automation. The ammonia concentrations are retrieved by fitting the second harmonic (2f) spectra, so theoretically the precision should be the same as traditional 2f detection. The accuracy is ensured by experimental calibrations of the spectroscopic parameters of both ammonia and ethylene, which are independent of ammonia concentrations. However, the accuracies of conventional calibration methods are limited by the uncertainties of ammonia standards, which can be quite large at ambient levels (ppbv) due to the adsorption effects of the gas delivery system. In long-term field measurements, frequent calibrations are usually needed to account for system drift. The traditional solution is by periodically calibrating the system with some standards, which can be expensive, labor-intensive, or subject to loss of measurement points. By checking the absorption signals of a fixed concentration reference cell, this in-situ calibration method enables continuous and unattended measurements, which are very important in rapidly changing conditions in the field.

System/Experimental Setup

A general system block diagram is shown in FIG. 1a. The system 20 includes a coherent (e.g., laser) light source 22 configured to transmit an interrogation light beam along an optical sample path 23 to a spectroscopic evaluation region (sample cell 24) including a substance for evaluation. The system 20 also includes an in-line reference cell 25 located in the optical sample path 23. The system 20 also includes a detector 26 having outputs 27 responsive to absorption signals from the sample 24 and the in-line reference cell 25. The detector is coupled to a processor 28 as generally shown by reference number 27. It should be understood that the detector outputs may be separately processed, e.g., demodulated, filtered and digitized, prior before being coupled to the processor 28. The processor 28 is configured to isolate reference absorption signals from the in-line reference cell 25 and sample absorption signals from the sample cell 24 and generate calibration information based on the reference absorption signals and generate a spectroscopic representation of the sample based on the sample absorption signals. By placing the in-line reference cell (that has a gas that absorbs within the laser tuning range) in the optical sample path, the system can continuously calibrate the sample signal of interest and normalize against other forms of drift or noise. The specific position or order of the sample cell and the reference cell may be varied or swapped.

Figure 1B:
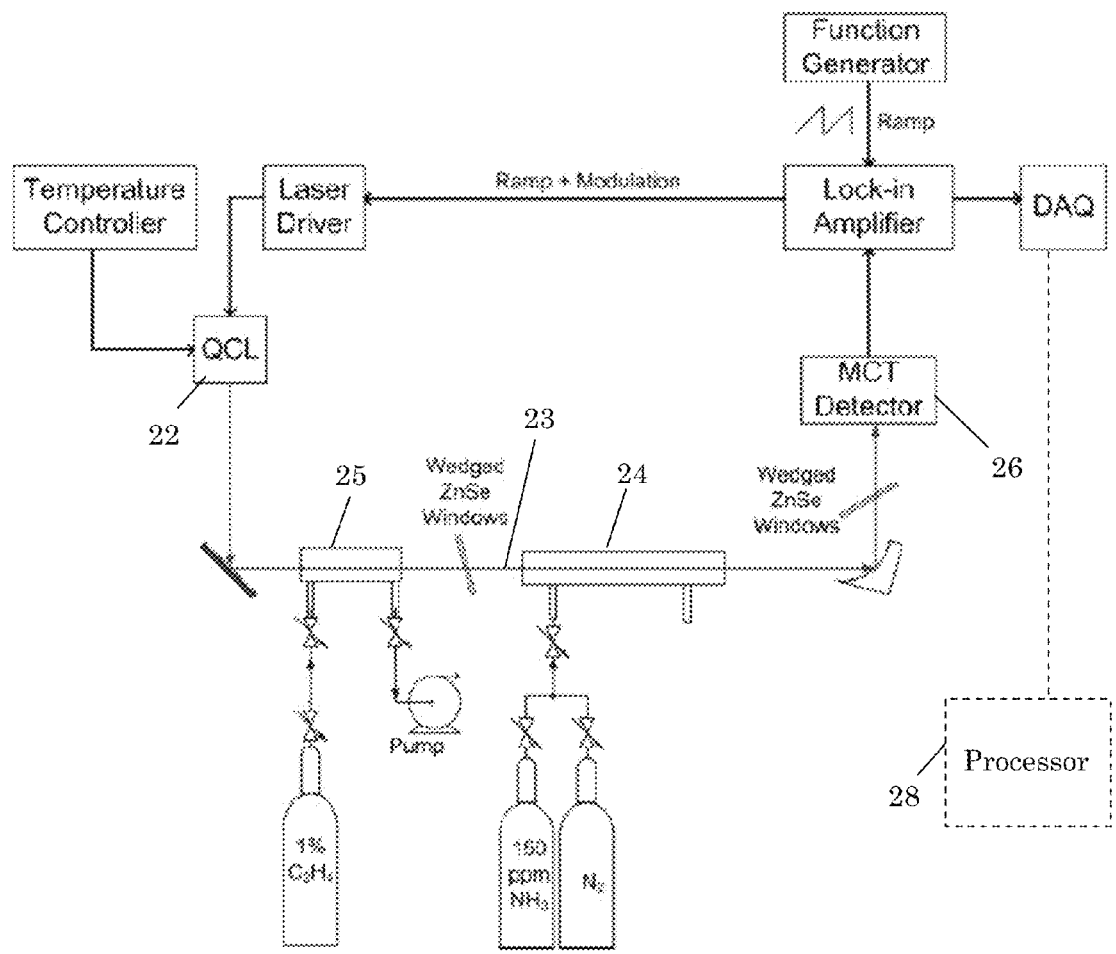
FIG. 1b is a block diagram of an experimental setup.

An experimental setup is depicted in FIG. 1b. In general, the two cells in series are filled with ethylene/nitrogen (reference cell 25) and ammonia/nitrogen (sample cell 24), respectively. The pressures in both cells can be controlled, and the ammonia can be diluted by nitrogen. The coherent or laser light source 22 includes circuitry configured to tune the coherent light source across an absorption range of interest and the coherent light source is scanned across the absorption range at a lower frequency and modulated at a higher frequency. In this example, a thermo electric (TE) cooled DFB quantum cascade laser (QCL) from Alpes Lasers is used. The laser temperature is stabilized by a thermoelectric temperature controller (Wavelength Electronics, HTC3000) and operated in continuous wave mode with a low noise laser diode driver (Wavelength Electronics, QCL500). The laser injection current is scanned across the absorption feature by a sawtooth ramp at 33 Hz and sinusoidally modulated at 10.37 kHz. The modulation depth of the QCL is calibrated using the method reported by Tao et al. The laser beam travels through two gas cells 25, 24 in series and is focused onto a TE-cooled photovoltaic MCT detector 26 (Vigo). The detector may be configured to respond proportionally to the amount of coherent light reaching it. A preamplifier circuit may also be used to amplify the detector output to enhance the signal-to-noise ratio. Two wedged ZnSe windows are put in the optical train to suppress etalons and avoid saturating the detector.

Figure 1C:
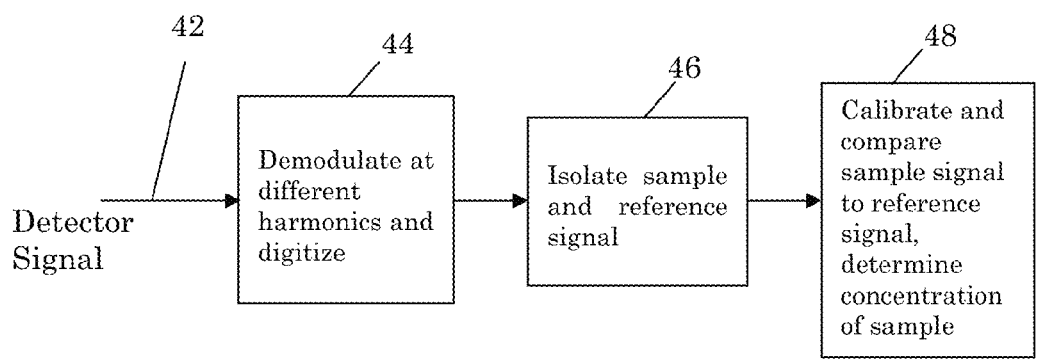
FIG. 1c is a block diagram showing the general processing steps.

The processor is configured to analyze a harmonic of the reference absorption signals (e.g., sixth or greater harmonic). The processor is also configured to analyze a harmonic of the sample absorption signals (e.g., a second harmonic of the sample absorption signals). FIG. 1c is a block diagram showing the general processing steps. Referring to FIGS. 1b and 1c in this example the analog detector signal is passed to a digital lock-in amplifier that can demodulate at three different harmonics simultaneously (Zurich Instruments, HF2). In this example, the digital lock-in amplifier is physically separate from the processor 28. It should be understood that such processing can also be implemented by processor 28 and can be considered part of the processing carried out by processor 28. The WMS signals output from the lock-in amplifier are collected on a National Instrument DAQ system (NI USB 6251, 16-bit, 1 MS/s). See FIG. 1c block 44. The reference absorption signals are offset spectrally from the sample absorption signals. The processor is configured to isolate the sample and reference signals as shown by block FIG. 1c block 46. As noted above, the system can continuously calibrate the sample signal of interest and normalize against other forms of drift or noise. Accordingly, the processor is configured to calibrate based on the reference absorption signal and determine the concentration of the sample as shown by block 46. The techniques used to determine the concentration of a gas under test based on absorption signals are well known. See for example the article by Joel A. Silver, "Frequency-modulation spectroscopy for trace species detection: theory and comparison among experimental methods" Applied Optics, Vol. 31, No. 6, pp 707-717, February 1992, which is incorporated herein in its entirety.

In this example, the reference cell 25 (L=10 cm) is filled with 1% ethylene in nitrogen (Air Liquide with accuracy of analysis±2%). The sample cell 24 (L=20 cm) is filled with 150 ppmv ammonia in nitrogen (Air Liquide with accuracy of analysis±10%) and can be diluted with dry nitrogen. The pressure of either cell can be controlled by a vacuum pump and is measured by an MKS pressure gauge with a full-scale reading of 1315 hPa (1000 Torr) and an accuracy 0.5% of reading. Either cell can be readily removed from the system to measure ethylene or ammonia absorption signals individually. The open-path ammonia sensor prototype described below differs only in that the sample cell is replaced by an open-path cylindrical multi-pass cell with a path length of 40 m.

Simulation of WMS Signals

In order to interpret and predict the multi-harmonic signal from the reference cell, a numerical model was developed based on the general WMS theories. The equations are rewritten to involve more variables for open-path atmospheric measurements. An infinite impulse response (IIR) filtering algorithm enables a direct comparison between the model and the signal output from a lock-in amplifier.

The injection current to the QCL can be written as a function of time, with a DC value:

$$i(t) = i_R R(2\pi f_R t) + i_m \cos(2\pi f_m t) + DC \quad (1)$$

where $R(2\pi f_R t)$ represents the sawtooth ramp function with $f_R$. $i_R$ and $i_m$ are the amplitude of the current ramp and sinusoidal modulation (with a frequency $f_m \gg f_R$), respectively. The current modulation leads to modulation of the laser light frequency near a constant frequency $v_0$. The laser light frequency, $v(t)$, is then given by:

$$v(t) = i_R \eta_R R(2\pi f_R t) + i_m \eta_m \cos(2\pi f_m t + \phi) + v_0 \quad (2)$$

where $\eta_R$ and $\eta_m$ are the current-to-frequency tuning rate at the ramp frequency and modulation frequency, and ø represents the phase difference between the modulated laser frequency and laser intensity. $i_m \eta_m$ defines the modulation depth. $\eta_R$, $\eta_m$ and $\phi$ are measured experimentally using the methods described in Tao et al.

According to the Beer-Lambert law, the laser intensity on the detector is:

$$I_1(t) = I_0(t) \exp\left[-\sum_i \sum_j \tau_{i,j}(v)\right] \quad (3)$$

Where $\tau_{i,j}(v)$ represents the optical depth generated by absorption line j of absorber i, $I_0(t)$ is the laser intensity, simulated by a polynomial function of injection current, and v=v(t) (see equation (2)). For a specific absorption line, the optical depth ti is given by:

$$\tau(v) = n S f(v) L \quad (4)$$

Here n is the number density of the absorber, L is the optical path length, and S is the line strength of this absorption line. $f(v)$ is the Voigt line shape function, following the formula given by Schreier:

$$f(v) = \frac{y}{\sqrt{\pi}\, \gamma_{col}} \text{Re}[W(x+yi)] \quad (5)$$

Where $$x = \frac{\sqrt{\ln 2}\,(v-v_0)}{\gamma_{Dop}},\ y = \sqrt{\ln 2}\,\frac{\gamma_{col}}{\gamma_{Dop}}\ \text{and } \text{Re}[W(z)]$$

and Re[W(z)] denotes the real part of the complex error function. $\gamma_{Dop}$ is the Doppler line width (HWHM), which is a function of temperature and molecular weight. $\gamma_{col}$ is the collision line width (HWHM) which is dependent on temperature, pressure, and foreign gas. When collision broadening is dominant, the modulation index is calculated as the ratio between modulation depth and the collision line width. Voigt line width is used for ethylene absorption at low pressure.

Substituting equation (2), (4), and (5) into equation (3), we derive the simulated detector signal $I_1$ which is only a function of time. Then we simulate the function of a lock-in amplifier by multiplying the detector signal with a reference sinusoidal signal at different harmonics of modulation frequency ($N_f$) to shift the targeted harmonic components to DC. An infinite impulse response (IIR) low-pass Butterworth filter is then applied to acquire the Nth harmonic WMS signal. The filter order and bandwidth need to be deliberately chosen to eliminate as much noise as possible and avoid signal distortion in the meantime. The simulated in phase $N_f$ signal is thus given by:

$$X(t,N)=\text{IIR}(I_1(t)\cos(2\pi N f_m t)) \quad (6)$$

For a single absorption line, the line center value of the Nth harmonic WMS signal is then denoted by X(linecenter, N).

Spectroscopic Calibration

In order to use ethylene as a reference absorption signal to calibrate ammonia, precise knowledge of the absorption cross-sections of both ammonia and ethylene is critically important. For instance, a variation in the relative line strengths of ammonia or ethylene of 10% leads to a direct variation of 10% on the ammonia concentration retrieval. The spectroscopic parameters that determine the absorption cross-section are given by the HITRAN database. However, HITRAN data can have large uncertainties and sometimes differ significantly from experimental validation. For example, the uncertainties of HITRAN ammonia line strengths are estimated to be 10-20%, and there are no reported uncertainties for the parameters of ethylene. The spectroscopic parameters for both ethylene and ammonia were re-measured precisely using direct absorption, 2f, and 4f signals.

Figure 2:
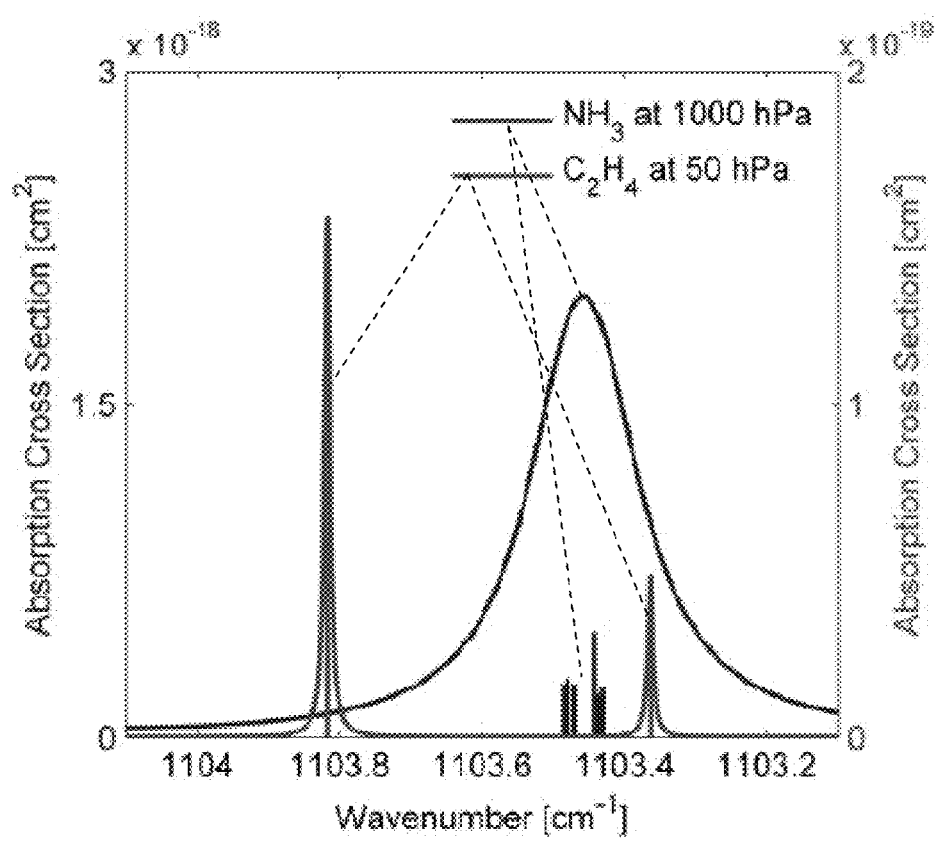
FIG. 2 is a graph showing HITRAN absorption lines of ammonia at ambient pressure (1000 hPa) and absorption lines of ethylene at reduced pressure (50 hPa)

The absorption features of six ammonia lines at atmospheric pressure and two nearby ethylene lines at reduced pressure are shown in FIG. 2 based on HITRAN spectroscopic parameters. The ethylene absorption line centered at 1103.3635 cm$^{-1}$ (9063.2 nm) is used as an inline reference absorption signal. An adjacent ethylene line centered at 1103.8174 cm$^{-1}$ (9059.5 nm) is also studied in the spectroscopic calibration. The ammonia absorption feature, which is a composite of six individual lines on the R branch of the v2α band, sR(6,1)-sR(6,6), is located between these two ethylene lines. Each individual ammonia line can be resolved and calibrated at low pressure (≤30 hPa).

Figure 3:
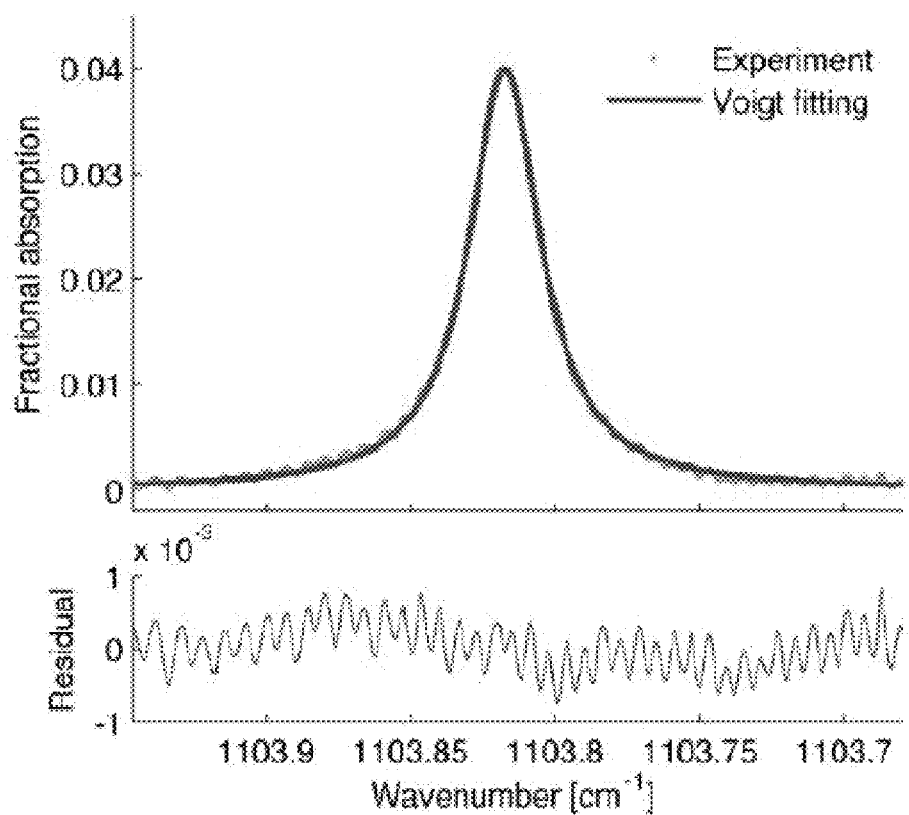
FIG. 3 is a graph showing ethylene absorption line at 1103.8174 $cm^{-1}$ measured with the QCL direct absorption spectroscopy at 200 hPa.

A nonlinear least squares fitting method was used to acquire the line shape parameters of ethylene. The ethylene absorption features of interest can be easily isolated by reducing the pressure below 500 hPa. First, the experimental direct absorption spectra are obtained by subtracting the absorbed signal $I_1(t)$ from the background signal $I_0(t)$ obtained by purging the cell with dry nitrogen. Only the current ramp is applied to the laser to sweep across the absorption line. A Germanium Febry-Perot etalon signal with a free spectral range of 0.04913 cm$^{-1}$ is used to calibrate the laser wavelength scale. During the Voigt fitting procedure using equation (5), the experimental parameters (temperature, pressure, mixing ratio, path length) are fixed to the measured or stated values. The spectroscopic parameters that have little impact on the experimental spectra (self broadening, temperature dependency exponent, lower state energy) are adopted from HITRAN 2008 database. Only collision line width and line strength are fitted. An experimental ethylene spectrum at 200 hPa with the Voigt fitting is shown in FIG. 3. The ethylene line strengths extracted from the fit fully agree with HITRAN values with residuals<2% of the peak absorption. However, the collision line widths are 15% smaller than the air-broadened collision line width given by HITRAN 2008.

Figure 4A:
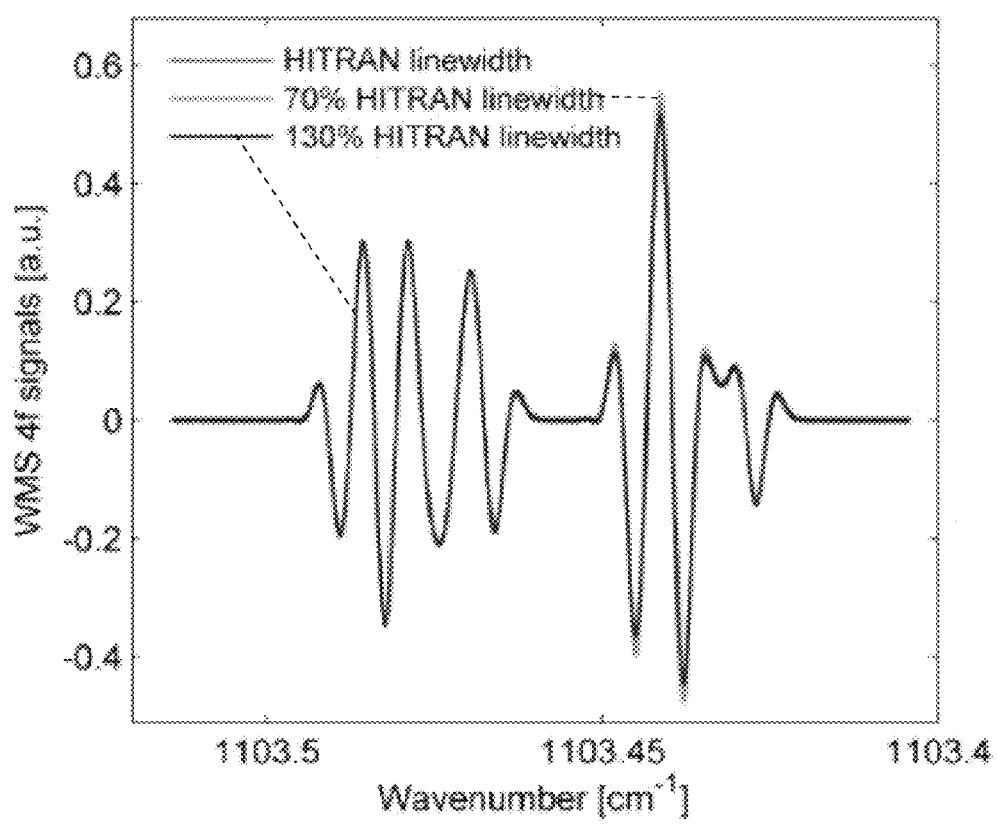
FIG. 4(a) is a graph showing simulation of ammonia 4f signal at 2 hPa by the numerical WMS model based on HIT- RAN 2008 parameters (red) and the collision line width of the sR(6,3) line centered at 1103.4412 cm$^{-1}$ is changed by ±30% artificially (blue and green)
Figure 4B:
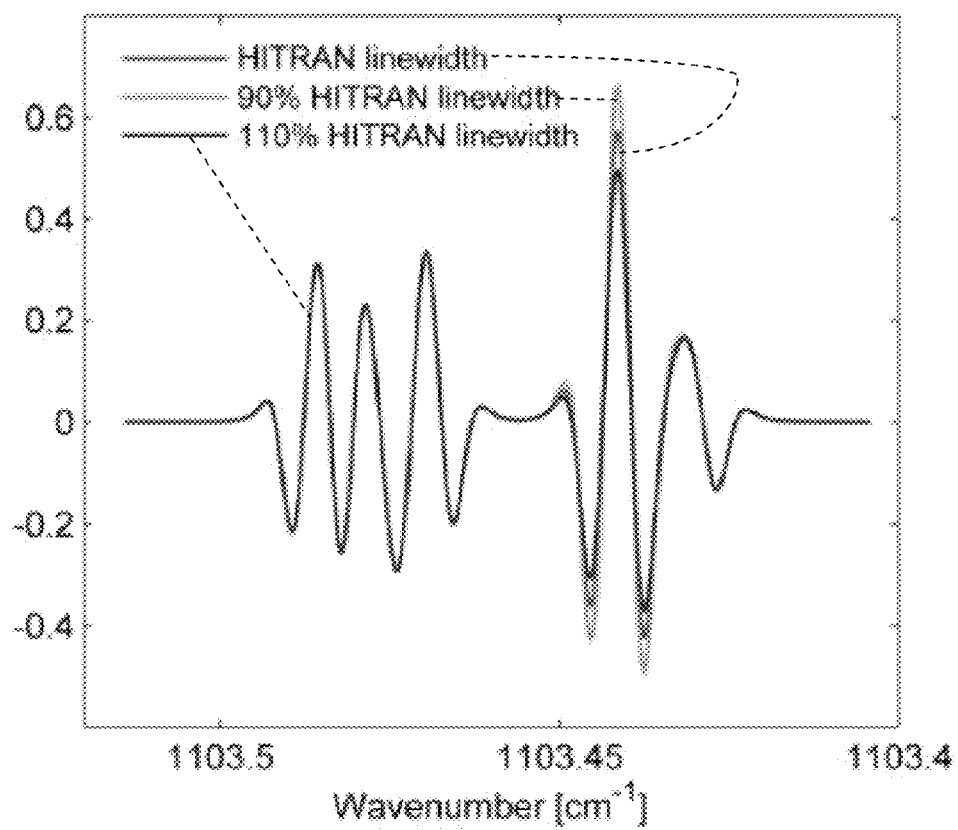
FIG. 4(b) is a graph showing simulation of ammonia 4f signal at 30 hPa (red) and the collision line width of the sR(6,3) line centered at 1103.4412 cm$^{-1}$ is changed by ±10% artificially (blue and green)

Comparing to direct absorption spectra, WMS signals can resolve congested absorption features and reveal more detailed line shape structure, especially for higher harmonics. The line strength and collision line width are measured in two steps. First, the pressure in the cell is reduced to 2 hPa. At this pressure, ammonia lines are essentially in Doppler line shape and resolved to the largest extent. Uncertainties coming from collision line widths are negligible in this case, which is shown in FIG. 4(a). To demonstrate this, the collision line width of the absorption line centered at 1103.4412 cm$^{-1}$ (sR(6,3)) is changed by ±30% artificially, but the 4f peak to trough height only changes by ±3%. Since the Doppler line width is well known, line strength is the only parameter to be characterized. Under this experimental condition, the contribution of line strength to WMS signal magnitude is essentially linear, so the line strength calibration is straightforward. Once the line strengths are measured, the collision line width is the only parameter to be determined. In the second step, the pressure in the cell is set to 30 hPa, at which the collision broadening is significant and the six lines are still resolved to a large extent. A similar sensitivity study is shown in FIG. 4(b). When the collision line width of the same transition (sR(6,3)) is changed by ±10% artificially, the 4f peak trough height changes by ±15%. In other words, any discrepancies in collision line width are amplified on 4f signal under this experimental condition.

Figure 5A:
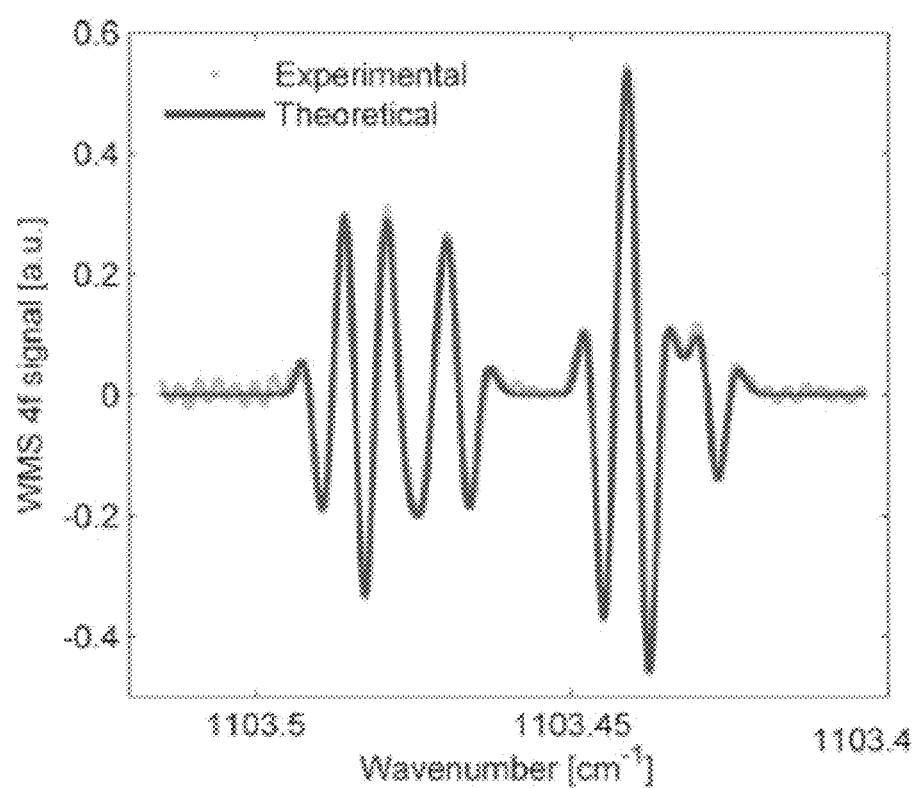
FIG. 5(a) shows the experimental (green dots) and simulated (red lines) ammonia 4f spectra at 2 hPa.
Figure 5B:
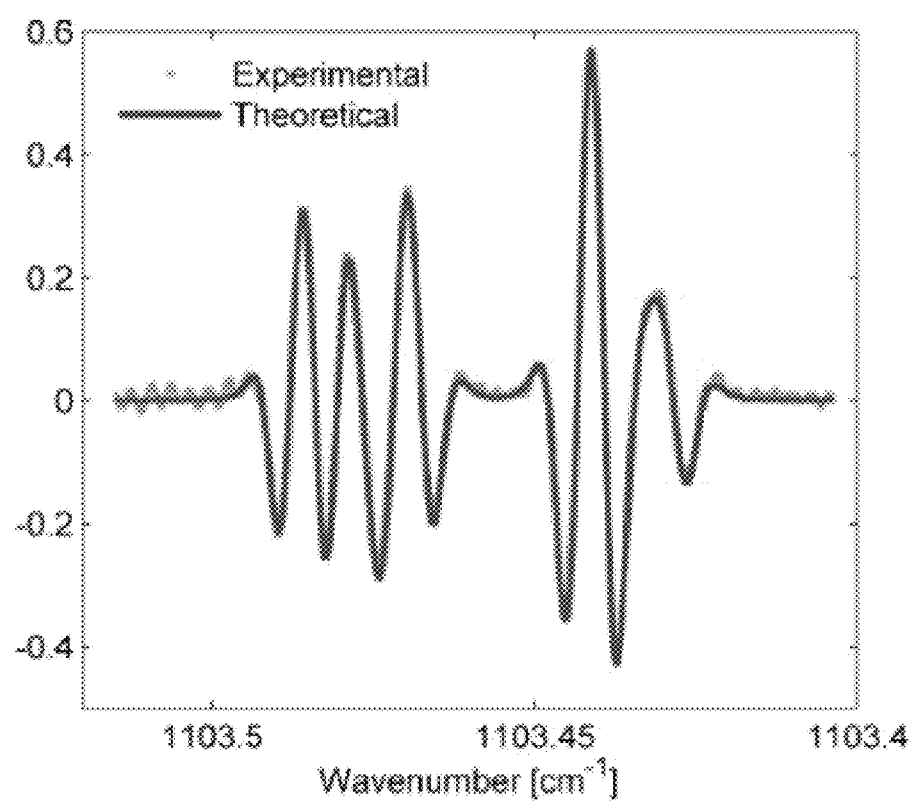
FIG. 5(b) shows the experimental (green dots) and simulated (red lines) ammonia 4f spectra at 30 hPa.

The experimental ammonia 4f spectra at these two pressures are presented in FIG. 5, compared with model simulation. The ammonia line strengths and collision line widths are adopted from HITRAN 2008 database. At 2 hPa, the simulation agrees with the experimental 4f spectrum within 5% for the six ammonia lines. At 30 hPa, the simulation agrees with the experimental 4f spectrum within 10% for the six ammonia lines.

The ethylene and ammonia spectroscopic calibrations generally agree with the HITRAN 2008 database. The only exception is the ethylene collision line width, which we measure to be 15% lower than HITRAN for both lines. The uncertainties for line strength measurements mainly come from the uncertainties of the concentration of the gas mixture we use (2% for ethylene and 10% for ammonia). The accuracy of this calibration method is 20%, according to propagation of errors of the gas concentration and spectral fitting.

Ammonia Calibration Using an Inline Ethylene Reference Cell

An inline calibration cell with a reference gas has been used in laser spectroscopy with isolated lines, but there are significant challenges when the reference absorption line overlaps with the target absorption line. The reference absorption signals are offset spectrally from the sample absorption signals. As shown in FIG. 2, one ethylene absorption line (even under reduced pressure) sits on the shoulder of the ammonia absorption feature. Due to the constraint of QCL tuning rate, we also need to use this ethylene line for calibration.

Figure 6:
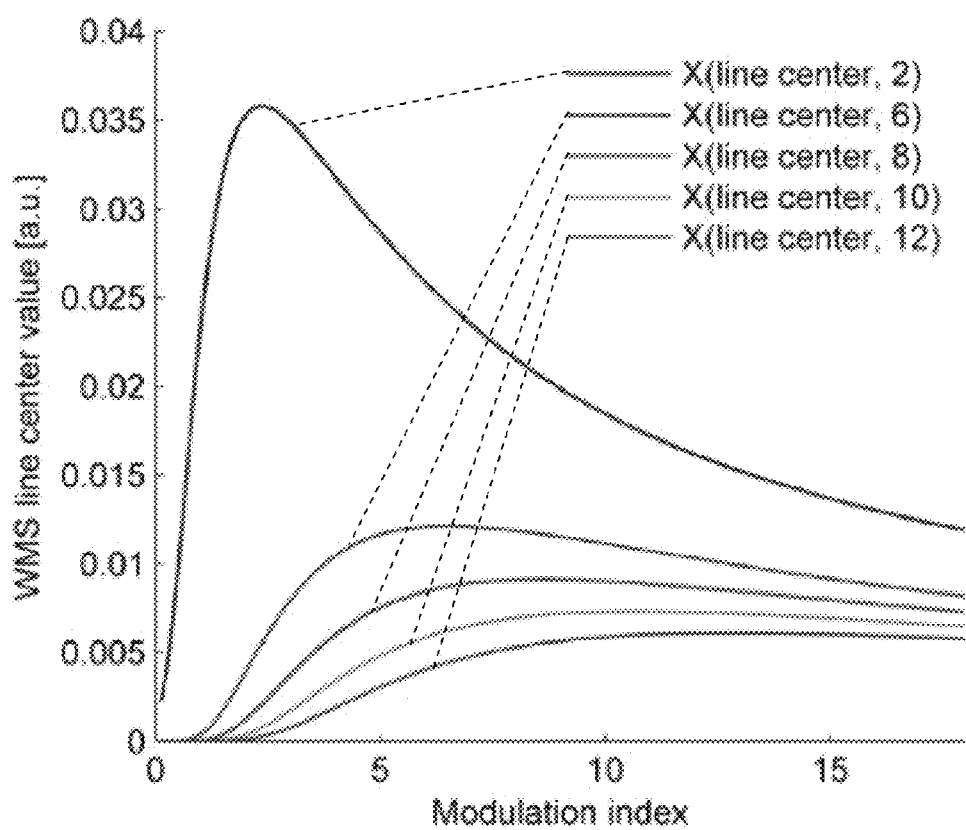
FIG. 6 is a graph showing the line center value of different harmonic WMS signals as a function of modulation index. Voigt profile is adopted here, but the results for Lorentzian profile show little difference.

FIG. 6 shows the simulated line center values of the Nth in phase harmonic signal (X (line center, N)) as a function of modulation index. In this example, the reference cell has a pressure of less than atmospheric pressure. The Voigt line width of the reference ethylene signal below 100 hPa is more than 10 times smaller than the Voigt line width of ambient ammonia absorption. Hence for the same modulation depth, the modulation index for ethylene under reduced pressure is more than 10 times larger than that of ambient ammonia (e.g., a reference cell pressure of approximately 0.1 atmospheres).

By deliberately choosing the modulation depth and the reference cell pressure, we can maximize the ethylene and ammonia signal at the same time by using different harmonics. A general rule of thumb is that the line center value of the Nth harmonic reaches its maximum at modulation index around N. For example, the modulation index to maximize 2f signal is 2.2. However, constrained by the limited tuning rate of the QCL (~0.006 cm$^{-1}$/mA) and the broad/congested atmospheric pressure ammonia peaks (HWHM~0.1 cm$^{-1}$), we cannot reach the optimal modulation index for ammonia. In this study we only use a modulation index of less than 0.5 for ammonia, which still gives a sufficient ambient ammonia 2f signal. Note that in FIG. 6, at a modulation index of 0.5, the ambient ammonia high harmonic signals are close to 0 for N~6. In the meantime, the modulation index for the ethylene line under reduced pressure is much larger and can be controlled through reference cell pressure to maximize the high harmonic signals. The 2f ethylene signal is extremely overmodulated and flattened, yielding little interference with 2f ambient ammonia signal.

FIG. 7 illustrates the 2f and 6f signals of ambient pressure ammonia and the reduced-pressure ethylene cell. In the experiment spectra shown in panel (a) and (b), the pressure in the ethylene reference cell is changed from 0 to 90 hPa. The modulation index is 0.25 for ammonia and 6 for ethylene when reference cell pressure is 50 hPa. On the 2f spectrum, the ethylene signal is obvious but it only perturbs one trough of the ammonia 2f spectrum. Since it is constant on 2f, it can be readily addressed by the spectral fitting routine. The 2f line center value of ammonia is not influenced by ethylene in any case. On the 6f spectrum, the ammonia signal is completely invisible, but the ethylene signal is very clear.

Figure 7A:
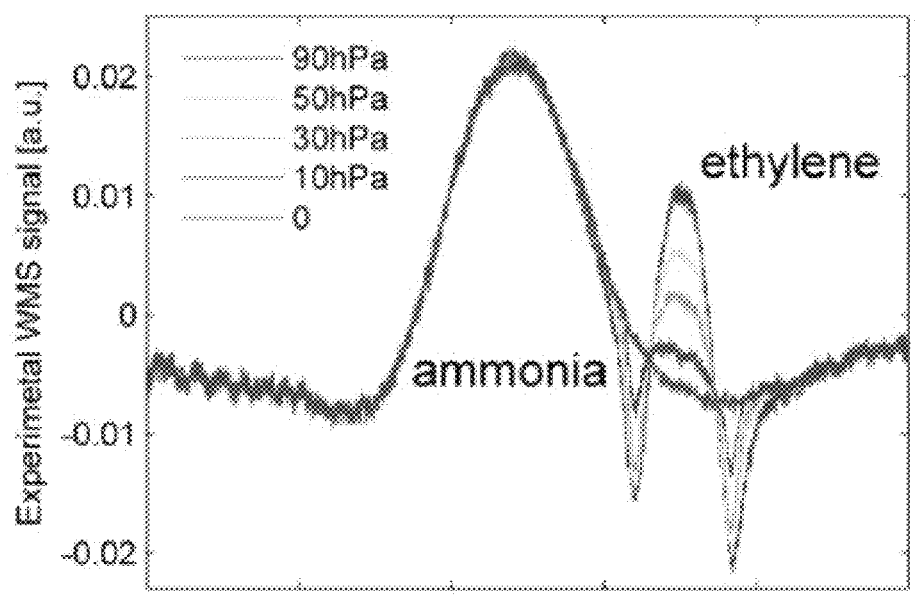
FIG. 7(a) and FIG. 7(b) show 2f and 6f spectra of ambient pressure ammonia and inline ethylene reference cell. The ethylene cell pressure is changed from 0 to 90 hPa.
Figure 7B:
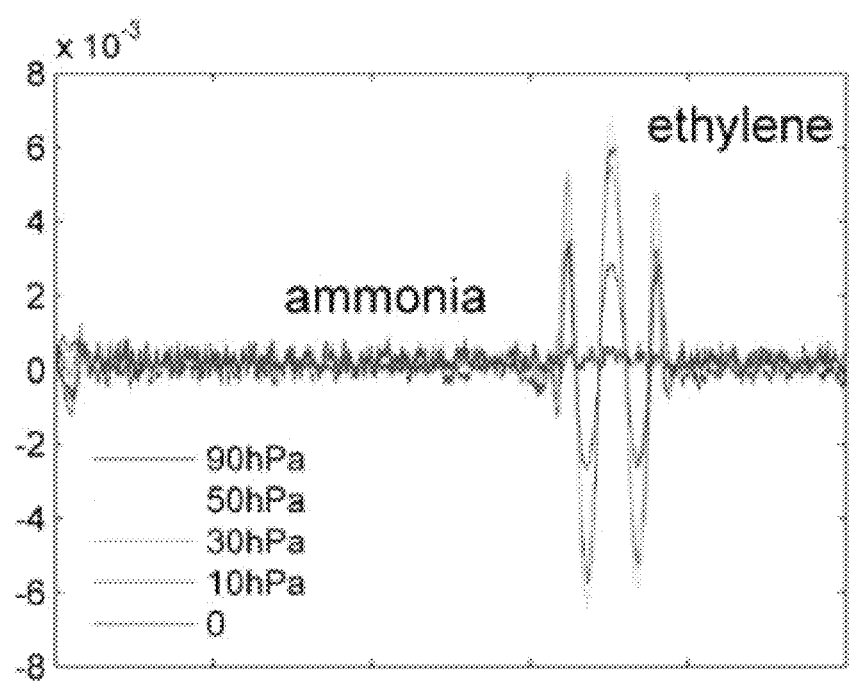
Figure 7C:
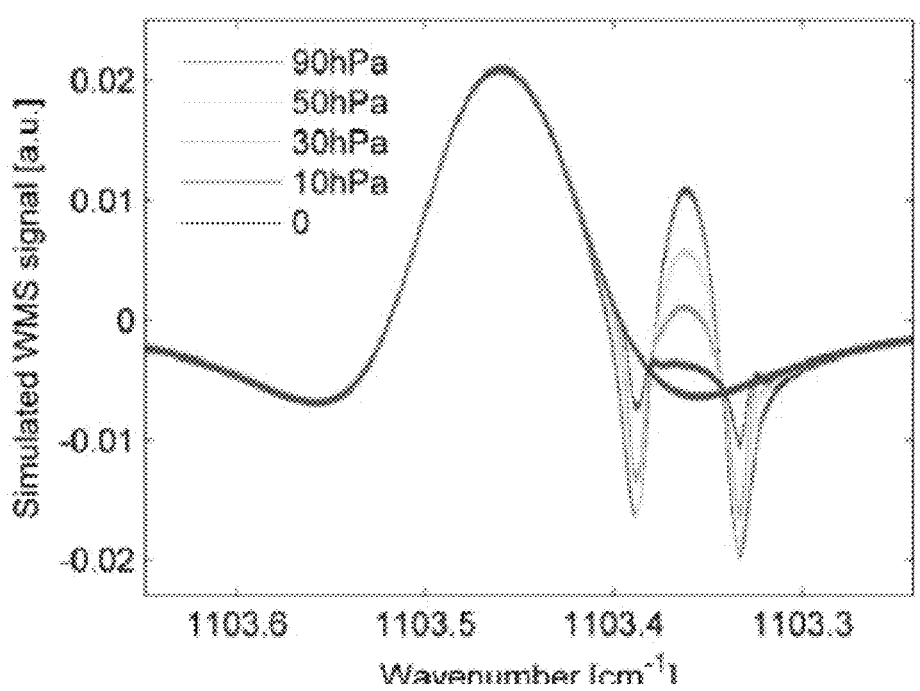
FIG. 7(c) and FIG. 7(d) show the simulation of the same experimental condition by the numerical WMS model.
Figure 7D:
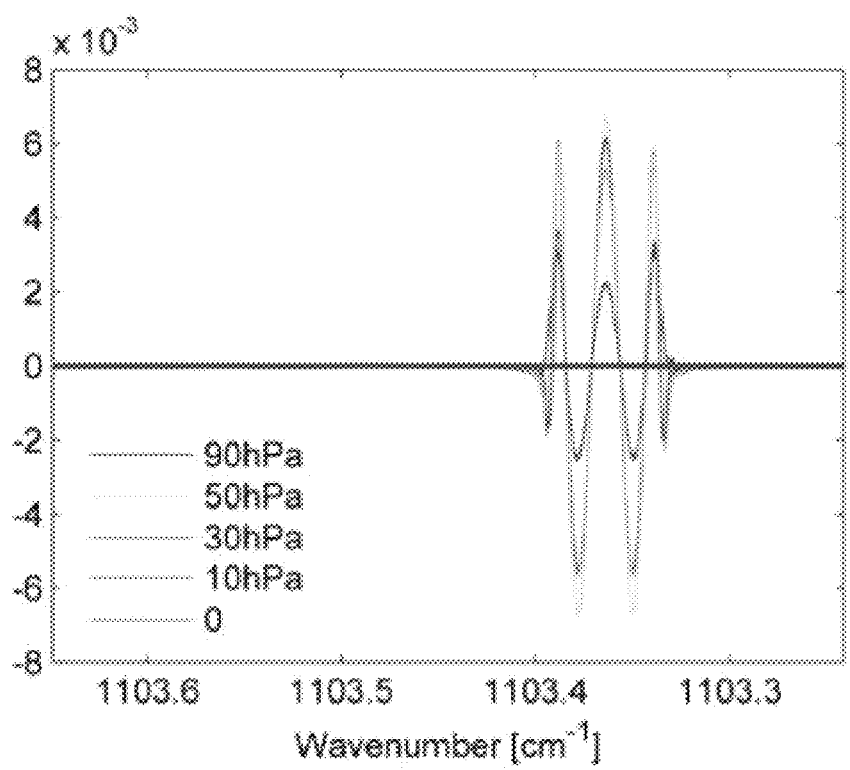

In FIGS. 7(c) and 7(d), the numerical WMS model is used to simulate the same conditions as the experiment. The concentration and pressure/temperature of ammonia and ethylene are fixed at the measured or stated values. The spectroscopic parameters are those from HITRAN 2008 except where we use our ethylene collision line width determined previously. The simulated 2f spectra are scaled to the same magnitude of the experimental 2f spectra, and the simulated 6f spectra are scaled using the same factor. The excellent agreement between experiment and simulation shows that the model can capture the relative values of different harmonic signals. It also indicates that we can fit the multi-harmonic spectra with the simulation results and retrieve ammonia concentrations.

FIG. 7 demonstrates that we are able to detect the ambient ammonia signal at 2f and the reference ethylene signal at high harmonic (6f in this case). In order to compare different high harmonics, we define r(N) as the ratio between the line center value of ethylene signal and the line center value of ammonia signal at the Nth harmonic:

$$r(N) = \frac{X_{ethylene}(\text{line center, } N)}{X_{ammonia}(\text{line center, } N)}$$

The ratio r(N) depends on the pressure of the ethylene reference cell and the modulation depth. We evaluate the ammonia signal at one harmonic $N_{NH3}$ and the ethylene reference signal at another harmonic $N_{ref}$. To ensure that changes in ambient ammonia don't influence the reference signal, it is necessary to minimize r($N_{NH3}$) and meanwhile maximize r($N_{ref}$). Here $N_{NH3}$=2 and $N_{ref}$ is one of the higher harmonics.

Figure 8A:
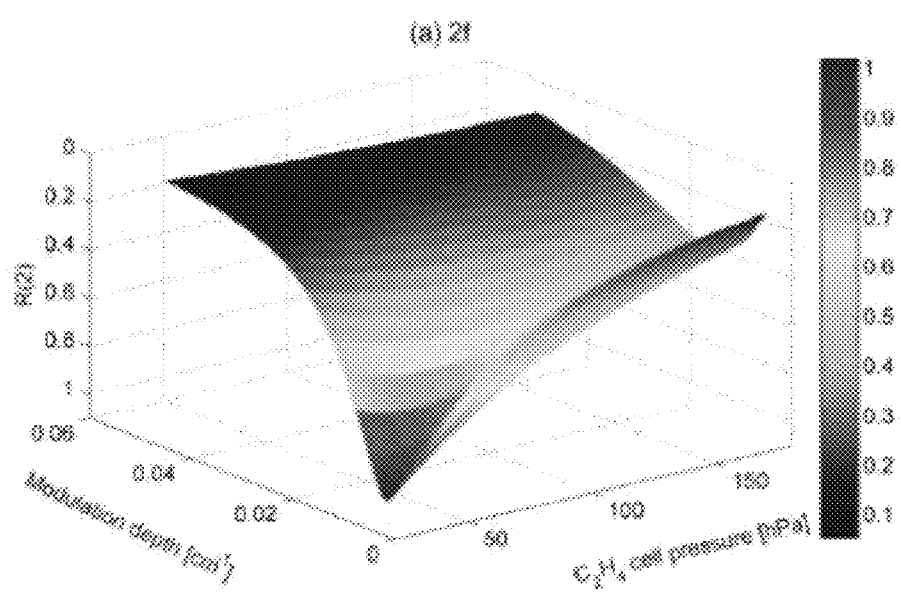
FIGS. 8(a)-8(c) are graphs showing r(N) as a function of modulation depth and ethylene cell pressure for N=2 (FIG. 8(a)), N=6 (FIG. 8(b)), and N=12 (FIG. 8(c)). The other parameters (ambient temperature, ethylene/ammonia concentration) are fixed at the experimental values in the simulation. The vertical axis of panel (a) is reversed because we want to minimize r(2) but maximize r(N) for N≥6.
Figure 8B:
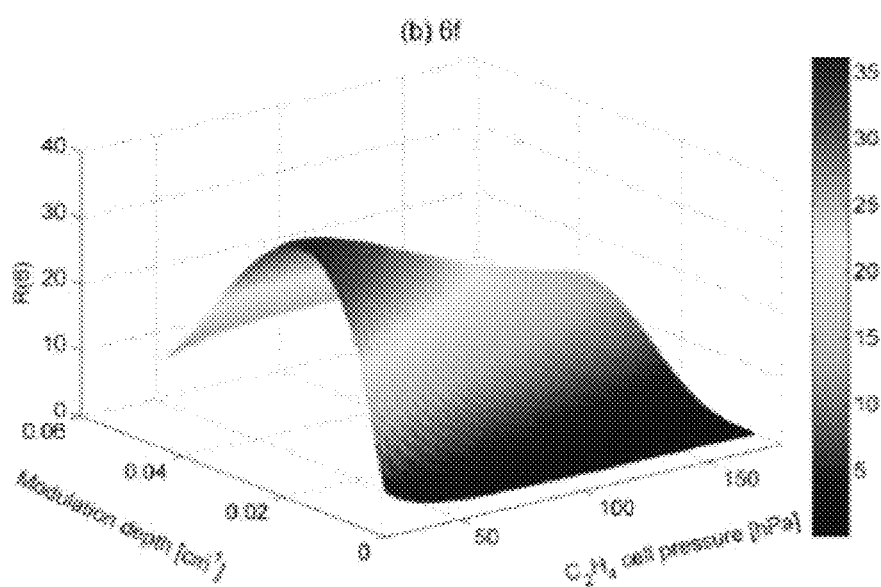

Consider $N_{ref}$=6. FIGS. 8(a) and 8(b) show r(2) and r(6) as a function of the modulation depth and pressure of ethylene reference cell. Note that in FIG. 8(a) the vertical axis is reversed because we want to minimize r(2). The maximized r(6) can be found near a modulation depth of 0.025 cm$^{-1}$ and an ethylene cell pressure of around 50 hPa. r(2) doesn't have a minimum for practical conditions, but at this modulation depth and ethylene cell pressure r(2) is small enough to not influence the ammonia signal.

Figure 8C:
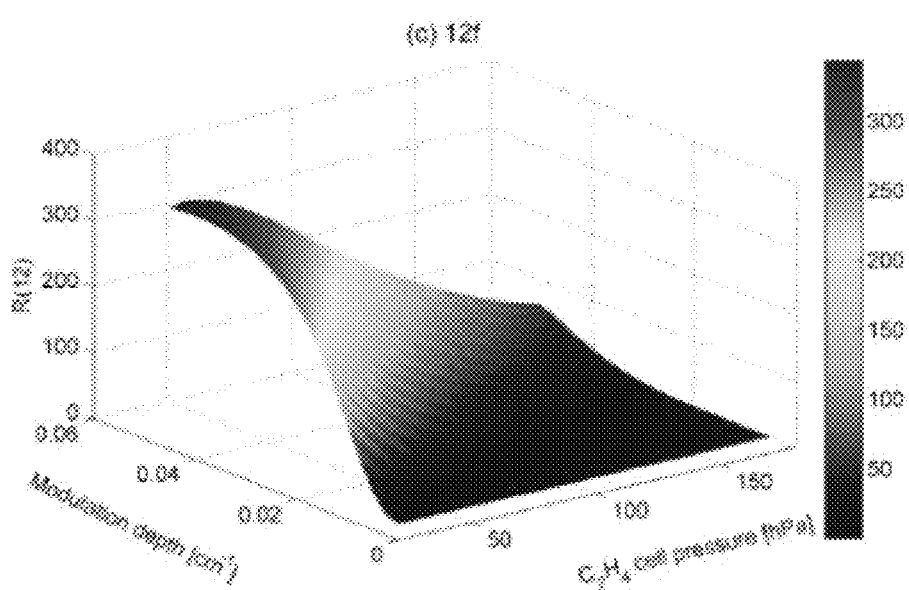

The maximum of r(6) occurs at a relatively small modulation depth, but FIG. 8(a) shows that r(2) keeps decreasing if the modulation depth increases. This implies that we can use even higher harmonics for the ethylene reference signal, so that the r(Nref) is larger and reaches its maximum at larger modulation depth. FIG. 8(c) investigates the ethylene/ammonia ratio at 12f. r(12) is about 400 under optimal conditions, indicating that the ammonia signal is vanishingly small compared to the ethylene reference signal at ultra high harmonics. At the same time, r(2) is much smaller when r(12) is maximized than it is when r(6) is maximized. This indicates a general trend that higher harmonic gives better separation between the ambient ammonia and reference ethylene signals. However, it will be ultimately limited by signal-to-noise ratio since the intensity decreases as N increases. The processor is configured to analyze a harmonic of the reference absorption signal. Generally, we use 6-12f depending on sensor configurations.

Figure 9:
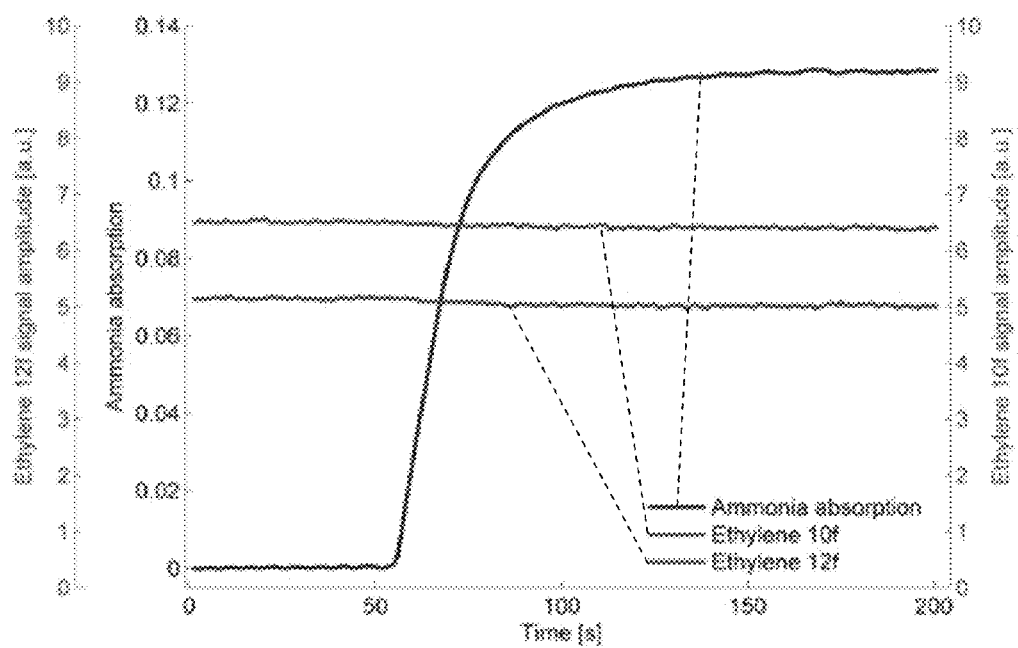
FIG. 9 is a graph showing time series of ammonia absorption (red), ethylene 10f signal (green) amplitude, and ethylene 12f signal amplitude (blue) when 150 ppmv ammonia was flowed into an ambient pressure cell filled with nitrogen.

According to the simulations shown in FIG. 8, the modulation depth and ethylene cell pressure were set to 0.05 cm$^{-1}$ and 50 hPa in the experiment, where r(12) is optimized. The ammonia cell was first purged by nitrogen and then filled with 150 ppmv ammonia. Ammonia concentrations are retrieved base upon spectral fitting using a LabVIEW-based program. Higher harmonic reference signals are fitted simultaneously with 2f, and signal amplitude obtained from the fitting is used as a scale factor to account for system drift. The outlet of the cell is open to the air to maintain ambient pressure. The lock-in amplifier can output three harmonics simultaneously, so 10f signals are also recorded. As shown by FIG. 9, when the ammonia concentration changes from 0 to about 150 ppmv (~13% absorption), the amplitudes of both 10f and 12f signals change by less than 2%. The precisions of both 10f and 12f reference signals are less than 1% (1σ). Since ambient ammonia absorption rarely reaches such a high level, we can conclude that the interferences of ambient ammonia on the high harmonic ethylene reference signals are negligible.

In polluted urban areas, ambient ethylene concentration may reach up to 30 ppbv, which gives a signal about 0.01% of the low-pressure ethylene reference signal at high harmonics. Hence the interferences from ambient ethylene are also negligible to the ethylene reference signal. Ambient ethylene may cause interferences to ambient ammonia signals at 2f when the ethylene concentration is >100 times higher than ammonia. However, these conditions are unlikely to happen and the signals can still be separated by spectral fitting.

Further description of the disclosed device is papers entitled "Inline Multi-harmonic Calibration Method for Open-path Atmospheric Ammonia Measurements", "Compact and portable open-path sensor for simultaneous measurements of atmospheric N$_2$O and CO using a quantum cascade laser", and "VCSEL-based calibration-free carbon monoxide sensor at 2.3 μm with in-line reference cell". These references are also part of the application and are incorporated by reference in their entirety as if fully set forth herein.

Any and all references listed herein are also part of the application and are incorporated by reference in their entirety as if fully set forth herein. It should be understood that many variations are possible based on the disclosure herein. Although features and elements are described above in particular combinations, each feature or element can be used alone without the other features and elements or in various combinations with or without other features and elements. The methods or flow charts provided herein may be implemented in a computer program, software, or firmware incorporated in a non-transitory computer-readable storage medium for execution by a general purpose computer or a processor. Examples of computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs)

What is claimed is:

1. A spectroscopic sensor having a sample cell containing a sample, the sensor comprising:
 a coherent light source configured to transmit an interrogation light beam along an optical sample path directed towards the sample;
 an in-line reference cell located in the optical sample path;
 a detector having outputs responsive to absorption signals from the sample and the in-line reference cell;
 a processor configured to isolate the reference absorption signals from the in-line reference cell and sample absorption signals from the sample cell and generate calibration information based on the reference absorption signals and determine a concentration of the sample based on the sample absorption signals; and
 circuitry configured to tune the coherent light source across an absorption range of interest and the coherent light source is scanned across the absorption range at a lower frequency and modulated at a higher frequency.

2. The sensor of claim 1 wherein the coherent light source is at least one of a quantum cascade laser, interband cascade laser, vertical cavity laser or semiconductor laser.

3. The sensor of claim 1 wherein the in-line reference cell is a closed path, in-line reference cell configured with angled windows or windows with an anti-reflective coating to minimize back reflections from the windows.

4. The sensor of claim 1 wherein the reference absorption signals are offset spectrally from the sample absorption signals.

5. The sensor of claim 1 wherein the reference cell has a pressure of less than atmospheric pressure.

6. The sensor of claim 5 wherein the reference cell has a pressure of approximately 0.1 atmospheres.

7. The sensor of claim 1 wherein the sample cell further comprises an optical cavity with an optical path length configured to measure the gas of interest at ambient conditions.

8. The sensor of claim 1 wherein the processor is configured to analyze a harmonic of the reference absorption signals.

9. The sensor of claim 8 wherein the processor is configured to analyze a sixth or greater harmonic of reference absorption signals.

10. The sensor of claim 1 wherein the processor is configured to analyze a harmonic of the sample absorption signals.

11. The sensor of claim 10 wherein the processor is configured to analyze a second harmonic of the sample absorption signals.

12. A spectroscopic method of determining a concentration of a sample cell containing a sample, the method comprising:
 providing a coherent light source configured to transmit an interrogation light beam along an optical sample path directed towards the sample;
 locating an in-line reference cell in the optical sample path; and
 detecting absorption signals from the sample and the in-line reference cell;
 isolating reference absorption signals from the in-line reference cell and sample absorption signals from the sample cell, generating calibration information based on the reference absorption signals and determining a concentration of the sample based on the sample absorption signals; and
 tuning the coherent light source across an absorption range of interest and scanning the coherent light source across the absorption range at a lower frequency and modulating the coherent light source at a higher frequency.

13. The method of claim 12 wherein the coherent light source is at least one of a quantum cascade laser, interband cascade laser, vertical cavity laser or semiconductor laser.

14. The method of claim 12 wherein the in-line reference cell is a closed path, in-line reference cell configured with angled windows or windows with an anti-reflective coating to minimize back reflections from the windows.

15. The method of claim 12 wherein the reference absorption signals are offset spectrally from the sample absorption signals.

16. The method of claim 12 further comprising pressurizing the reference cell at a pressure that is less than atmospheric pressure.

17. The method of claim 12 further comprising pressurizing the reference cell at approximately 0.1 atmospheres.

18. The method of claim 12 wherein the sample cell further comprises an optical cavity with an optical path length configured to measure the gas of interest at ambient conditions.

19. The method of claim 12 further comprising analyzing a harmonic of the reference absorption signals.

20. The method of claim 12 further comprising analyzing a sixth or greater harmonic of reference absorption signals.

21. The method of claim 12 further comprising analyzing a harmonic of the sample absorption signals.

22. The method of claim 21 further comprising analyzing a second harmonic of the sample absorption signals.

* * * * *